(12) United States Patent
Shute et al.

(10) Patent No.: US 11,583,196 B2
(45) Date of Patent: Feb. 21, 2023

(54) SYSTEMS AND METHODS FOR DETECTING ATRIAL TACHYARRHYTHMIA

(71) Applicant: Cardiac Pacemakers, Inc., St. Paul, MN (US)

(72) Inventors: Jonathan Bennett Shute, Minnetonka, MN (US); Sunipa Saha, Shoreview, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 426 days.

(21) Appl. No.: 16/803,672

(22) Filed: Feb. 27, 2020

(65) Prior Publication Data

US 2020/0288997 A1  Sep. 17, 2020

Related U.S. Application Data

(60) Provisional application No. 62/817,329, filed on Mar. 12, 2019.

(51) Int. Cl.
| | |
|---|---|
| *A61B 5/024* | (2006.01) |
| *A61B 5/0205* | (2006.01) |
| *A61B 5/08* | (2006.01) |
| *A61B 5/00* | (2006.01) |
| *A61B 5/11* | (2006.01) |
| *A61B 5/363* | (2021.01) |

(52) U.S. Cl.
CPC ........ *A61B 5/02405* (2013.01); *A61B 5/0205* (2013.01); *A61B 5/08* (2013.01); *A61B 5/4836* (2013.01); *A61B 5/686* (2013.01); *A61B 5/72* (2013.01); *A61B 5/725* (2013.01); *A61B 5/7246* (2013.01); *A61B 5/7282* (2013.01); *A61B 5/1118* (2013.01); *A61B 5/363* (2021.01); *A61B 5/4839* (2013.01)

(58) Field of Classification Search
CPC ..... A61B 5/02405; A61B 5/0205; A61B 5/08; A61B 5/4836; A61B 5/686; A61B 5/72; A61B 5/7246; A61B 5/725; A61B 5/7282; A61B 5/363; A61B 5/1118; A61B 5/4839
See application file for complete search history.

(56) References Cited

U.S. PATENT DOCUMENTS

| | | | |
|---|---|---|---|
| 7,678,061 B2 | 3/2010 | Lee et al. | |
| 2004/0092836 A1* | 5/2004 | Ritscher | G06K 9/00557 600/518 |
| 2004/0127804 A1 | 7/2004 | Hatlesad et al. | |
| 2006/0167364 A1* | 7/2006 | Houben | G06K 9/00557 600/515 |

(Continued)

*Primary Examiner* — Matthew Kremer
*Assistant Examiner* — Om Patel
(74) *Attorney, Agent, or Firm* — Schwegman Lundberg & Woessner, P.A.

(57) ABSTRACT

Systems and methods for detecting cardiac arrhythmia are discussed. An exemplary medical-device system includes an arrhythmia detector circuit that receives physiologic information, including respiration and heart beat information a patient, and determines whether a respiratory sinus arrhythmia (RSA) is present or absent using the respiration and the heart beat information. An indication of the presence or absence of RSA may be stored in a memory. The arrhythmia detector circuit can detect an AT episode using the indication of RSA.

20 Claims, 7 Drawing Sheets

(56) References Cited

U.S. PATENT DOCUMENTS

| | | | |
|---|---|---|---|
| 2013/0138002 A1* | 5/2013 | Weng | A61B 5/7228 600/508 |
| 2013/0190631 A1 | 7/2013 | Doerr | |
| 2016/0045125 A1 | 2/2016 | Krueger et al. | |
| 2016/0296123 A1* | 10/2016 | Plans Casal | A61B 5/0205 |
| 2017/0296076 A1* | 10/2017 | Mahajan | A61B 5/002 |
| 2018/0104502 A1 | 4/2018 | Perschbacher et al. | |
| 2018/0192902 A1 | 7/2018 | Perschbacher et al. | |

\* cited by examiner

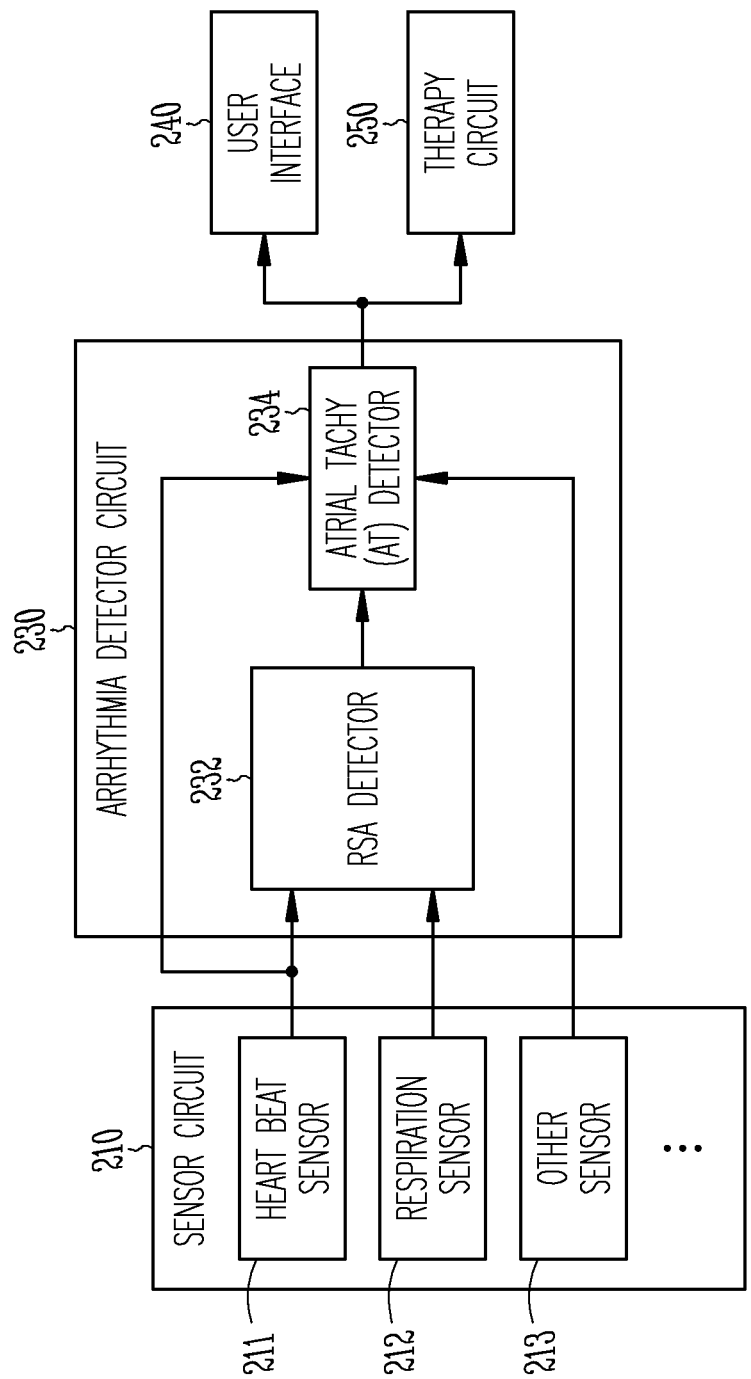

SYSTEMS AND METHODS FOR DETECTING ATRIAL TACHYARRHYTHMIA

CLAIM OF PRIORITY

This application claims the benefit of priority under 35 U.S.C. § 119(e) of U.S. Provisional Patent Application Ser. No. 62/817,329, filed on Mar. 12, 2019, which is herein incorporated by reference in its entirety.

TECHNICAL FIELD

This document relates generally to medical devices, and more particularly, to systems, devices and methods for detecting atrial tachyarrhythmia.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs can detect cardiac arrhythmias, such as atrial tachyarrhythmia (AT). One type of AT is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself. Persistent AF may last for over a week and typically requires medication or other treatment to revert to normal sinus rhythm. AF is permanent if a normal heart rhythm cannot be restored with treatment. AF may be associated with stroke and requires anticoagulation therapy.

Another type of AT is atrial flutter (AFL). AFL usually accompanies with some degree of atrioventricular (AV) node conduction block, and can be associated with a fast and usually regular heart rate. Typical or Type I AFL may involve a single reentrant circuit in the right atrium around the tricuspid valve annulus, and has an atrial rate of 240 to 340 beats per minute (bpm). The reentrant circuit most often travels in a counter-clockwise direction. Atypical or Type II AFL follows a different circuit, which may involve the right or the left atrium, and usually has a faster atrial rate of around 340-440 bpm. AFL may be associated with a variety of cardiac disorders, such as coronary artery disease (CAD) or hypertensive heart disease. AFL may often degenerate into AF. Prolonged fast AFL may lead to decompensation with loss of normal heart function. This may manifest as effort intolerance, nocturnal breathlessness, or swelling of the legs or abdomen.

Timely detection of AT may be clinically important for assessing cardiac function. Atrial tachyarrhythmia may be characterized by fast atrial rate and irregular ventricular rates. However, irregular ventricular rates can be a caused by confounding factors such as respiration-mediated sinus arrhythmia, and affect AT detection specificity. Inappropriate AT detection may have adverse impact on patient outcome.

OVERVIEW

This document discusses, among other things, systems, devices, and methods for detecting cardiac arrhythmias, such as an atrial tachyarrhythmia (AT). An exemplary medical-device system includes an arrhythmia detector circuit that can receive physiologic information of the patient, including respiration information and heart beat information concurrently acquired from a patient, and determine a respiratory sinus arrhythmia (RSA) indicator indicating a presence or absence of RSA using the received respiration information and the heart beat information. The arrhythmia detector circuit can detect an AT episode using the received physiologic information and the determined RSA indicator.

Example 1 is a medical-device system for detecting cardiac arrhythmia. The system comprises an arrhythmia detector circuit configured to receive respiration and heart beat information from a patient. The respiration and heart beats information may be concurrently acquired. The arrhythmia detector circuit can determine whether a respiratory sinus arrhythmia (RSA) is present or absent using the received respiration and the heart beat information, store an indication of the presence or absence of RSA, and detect an atrial tachyarrhythmia (AT) episode using the indication of RSA.

In Example 2, the subject matter of Example 1 optionally includes the arrhythmia detector circuit that can be configured to perform an initial AT detection using the received heart beat information, and confirm the initial AT detection if the RSA is absent, or reject the initial AT detection if the RSA is present.

In Example 3, the subject matter of Example 2 optionally includes the arrhythmia detector circuit that can be configured to receive the respiration and heart beat information concurrently acquired from the patient.

In Example 4, the subject matter of any one or more of Examples 2-3 optionally includes the arrhythmia detector circuit that can be configured to generate the initial AT detection using a physiologic signal distinct from, and concurrently acquired with, the received respiration and heart beat information.

In Example 5, the subject matter of any one or more of Examples 1-4 optionally includes the arrhythmia detector circuit that can be configured to use the indication of RSA to select a signal portion from the received heart beat information.

In Example 6, the subject matter of any one or more of Examples 1-4 optionally includes the arrhythmia detector circuit that can be configured to determine RSA indicators respectively for multiple temporally separated portions of the received respiration and heart beat information, identify from received physiologic information one or more portions corresponding to the RSA indicators indicating an absence of RSA, and detect the AT episode using the identified one or more portions of the received physiologic information.

In Example 7, the subject matter of any one or more of Examples 1-4 optionally includes the arrhythmia detector circuit that can be configured to filter received physiologic information to attenuate RSA interference using an RSA characteristic, and detect the AT episode using the filtered received physiologic information.

In Example 8, the subject matter of Example 7 optionally includes the arrhythmia detector circuit that can be configured to filter the received physiologic information using an adaptive filter.

In Example 9, the subject matter of any one or more of Examples 7-8 optionally includes the RSA characteristic that can include a heart rate variability.

In Example 10, the subject matter of any one or more of Examples 7-9 optionally includes the arrhythmia detector circuit that can be configured to generate the RSA characteristic under a specified patient condition including a specific posture, a specific physical activity, or a specific time of day.

In Example 11, the subject matter of any one or more of Examples 1-10 optionally includes the arrhythmia detector circuit that can be configured to adjust an AT detection criterion if the RSA is present, and to detect the AT episode using the adjusted AT detection criterion.

In Example 12, the subject matter of Example 11 optionally includes the AT detection criterion that can include a heart rate variability threshold. The arrhythmia detector circuit can be configured to increase the heart rate variability threshold if the RSA is present, or decrease the heart rate variability threshold if the RSA is absent.

In Example 13, the subject matter of any one or more of Examples 1-12 optionally includes an accelerometer sensor configured to sense the respiration information, and a cardiac activity sensor, separate from the accelerometer sensor, configured to detect heart beat from a cardiac signal of the patient.

In Example 14, the subject matter of any one or more of Examples 1-13 optionally includes the received respiration information that can include a respiration signal. The arrhythmia detector circuit can be configured to generate a heart rate (HR) signal using the received heart beat information wherein the HR signal including measurements of HR or cardiac cycle length over multiple cardiac cycles, and determine whether the RSA is present or absent using a correlation between the HR signal and the respiration signal.

In Example 15, the subject matter of Example 14 optionally includes the arrhythmia detector circuit that can be configured to determine a first RSA indicator of a presence of RSA if the correlation between the HR signal and the received respiration information is above a threshold, or a second RSA indicator of an absence of RSA if the correlation between the HR signal and the received respiration information is below the threshold.

Example 16 is a method of detecting atrial tachyarrhythmia (AT). The method comprises steps of: receiving respiration and heart beat information from a patient; determining whether a respiratory sinus arrhythmia (RSA) is present or absent using the received respiration and the heart beat information; and detecting an AT episode using the determined presence or absence of RSA.

In Example 17, the subject matter of Example 16 optionally includes detecting the AT episode that can include steps of: performing an initial AT detection using the received heart beat information; and confirming the initial AT detection if the RSA is absent, or reject the initial AT detection if the RSA is present.

In Example 18, the subject matter of any one or more of Examples 16-17 optionally include selecting from received physiologic information a signal portion using an indication of RSA presence or absence, and detecting the AT episode using the selected signal portion.

In Example 19, the subject matter of any one or more of Examples 16-18 optionally includes filtering received physiologic information to attenuate RSA interference using an RSA characteristic, and detecting the AT episode using the filtered received physiologic information.

In Example 20, the subject matter of Example 19 optionally includes the RSA characteristic that can include a heart rate variability under a specified patient condition including a specific posture, a specific physical activity, or a specific time of day.

In Example 21, the subject matter of any one or more of Examples 16-20 optionally include adjusting an AT detection criterion if the RSA is present, and detecting the AT episode using the adjusted AT detection criterion.

In Example 22, the subject matter of Example 21 optionally includes the AT detection criterion that can include a heart rate variability threshold, and the adjusting the AT detection criterion can include increasing the heart rate variability threshold if the RSA is present, or decreasing the heart rate variability threshold if the RSA is absent.

In Example 23, the subject matter of any one or more of Examples 16-22 optionally includes the received respiration information that can include a respiration signal. The method comprises steps of: generating a heart rate (HR) signal using the received heart beat information, the HR signal including measurements of HR or cardiac cycle length over multiple cardiac cycles; determining a correlation between the HR signal and the respiration signal; and determining a presence of RSA if the determined correlation is above a threshold, or an absence of RSA if the determined correlation is below the threshold.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 2 illustrates generally an example of an arrhythmia detection system configured to detect an arrhythmia episode, such as an AT episode.

DETAILED DESCRIPTION

Figure 1:
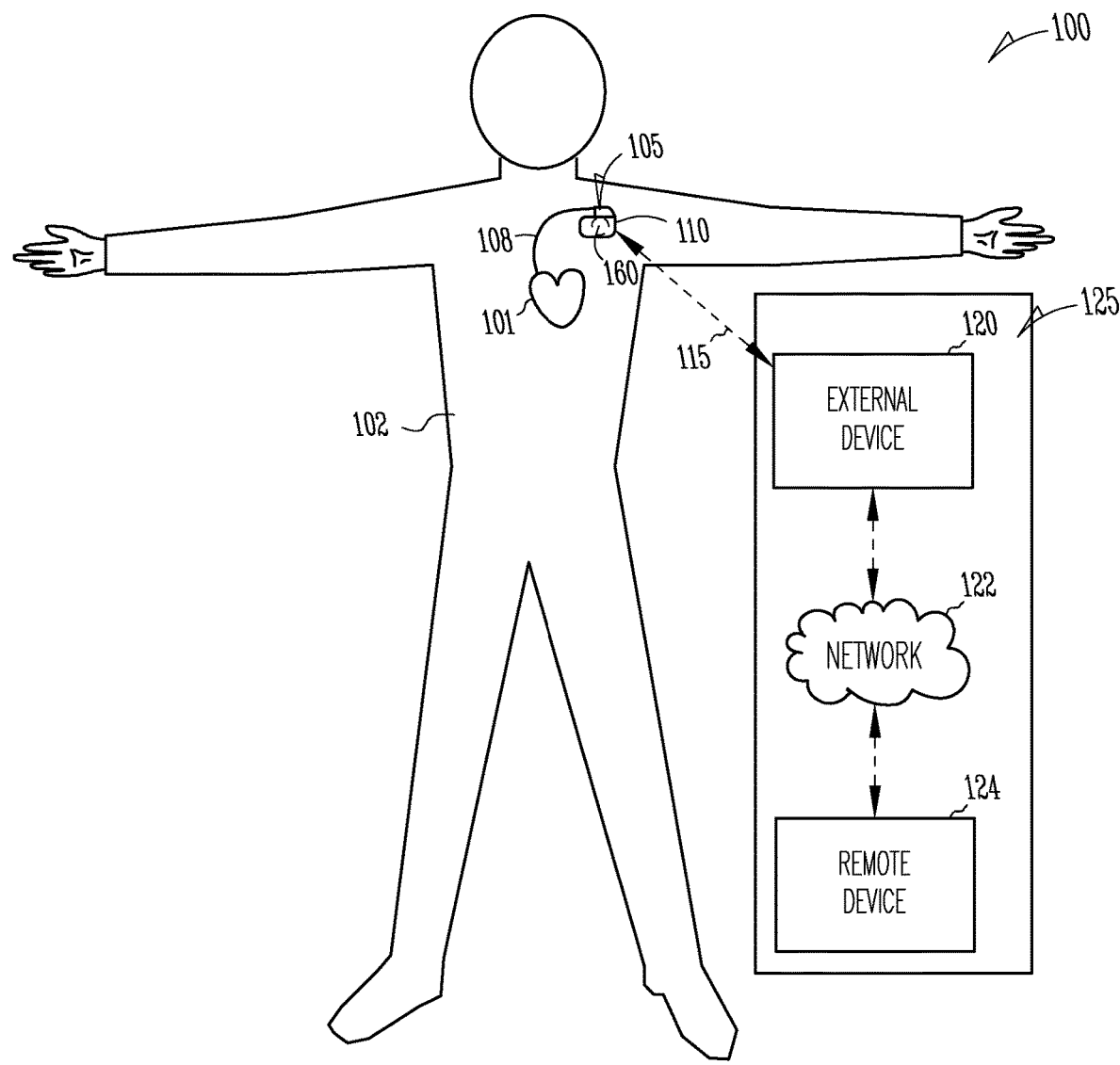
FIG. 1 illustrates generally an example of a patient management system and portions of an environment in which the system may operate.

Some IMDs are capable of detecting physiologic events, such as cardiac arrhythmias or progression of chronic heart diseases, and obtaining sampled values of cardiac electrical activity signals such as electrograms. Some IMDs may further be communicated with multiple physiologic sensors that may measure various physiologic signals. Capturing accurate electrogram or other physiologic sensor information obtained over a longer period of time, such as chronically between regularly-scheduled outpatient office visits, may help the physician re-program the device, if needed, diagnose cardiac disease, or assess the patient's health status.

Atrial tachyarrhythmia are characterized by fast atrial rate. In some patients, direct sensing of atrial activation rate with an electrode positioned in the atrium is not available or not feasible, such as patients not indicated for atrial lead implantation. A medical device, such as a single-chamber IMB with no dedicated atrial sensing/pacing lead, may detect the AT based on sensed ventricular activity (e.g., ventricular heart rates), instead of direct sensing of atrial activity from the atrium. At least due to the refractoriness of the AV node, ventricular rates can be irregular during AF or AFL, thus can be used to detect occurrence of an AT episode.

However, irregular ventricular rates can be caused by other confounding factors such as noise, motion artifacts, cardiac rhythms with a non-atrial origin, or vagus stimulation such as via baroreflex activation. For example, heart rates may be mediated by respiration, resulting in respiratory sinus arrhythmia (RSA). RSA is a naturally occurring variation in heart rate within a breathing cycle, which can be a result of baroreflex stimulation produced by changes in arterial pressure due to the regular inspiratory increase in venous return to the heart. During RSA, inhalation temporarily suppresses vagal activity, causing an immediate increase in heart rate. Exhalation, on the contrary, increases and resumes the vagal tone. Such an increase in vagal tone both slows the heart and makes heart rate more variable. While RSA is generally physiological and does not require treatment, a medical device may misrecognize an RSA event as an episode of AF or AFL at least based on the irregular ventricular rates, and triggers a false alarm. False positive AT detections due to RSA or other confounding factors can decrease the specificity of detecting AT, and lead to inappropriate and unnecessary interventions. On the other hand, a true AT episode may be misrecognized as a RSA or an aberrancy such as due to conduction abnormality at a bundle branch (e.g., rate-dependent bundle branch block), resulting in false negative AT detections.

Both false positive and false negative AT detections can adversely affect the device efficacy and unwarrantedly increase the healthcare cost associated with patient management. For example, false alarms of the inappropriately detected AT dues to RSA, or presenting to clinicians a large volume of inappropriately detected arrhythmic events for review or adjudication, may diminish the clinical utility of the AT detection feature in a medical device. False negative detections due to RSA or other confounding factors can decrease AT detection sensitivity, causing delay in necessary antiarrhythmic therapies or interventions. For at least these reasons, the present inventors have recognized, among other things, substantial challenges and a demand for a more efficient system and methods to distinguish AT from other events such as RSA.

Disclosed herein are systems, devices, and methods for detecting cardiac arrhythmia, such as an AT episode. An exemplary medical-device system includes an arrhythmia detector circuit that can receive physiologic information of the patient, including respiration information and heart beat information concurrently acquired from a patient, and determine a respiratory sinus arrhythmia (RSA) indicator indicating a presence or absence of RSA using the received respiration information and the heart beat information. The arrhythmia detector circuit can detect an AT episode using the received physiologic information and the determined RSA indicator.

The systems, devices, and methods discussed in this document may improve the medical technology of automated detection of atrial tachyarrhythmia and prevention of worsening of cardiac function. Recognition RSA indication, and using that information in detecting atrial tachyarrhythmia enhance the performance and functionality of an ambulatory cardiac device. For example, this document discusses, among other things, adjusting an AT detection criterion (e.g., a threshold) based on the RSA indication, or processing a physiological signal (e.g., filtering the signal or selecting a portion of the physiological signal) based on the RSA indication and detecting AT using the processed physiological signal. Compared to conventional AT detection techniques that rely on irregularity of heart rates, the detection of RSA using a respiration sensor separate from and independent of heart rate sensing can improve differential diagnosis between RSA and AT. Incorporation of the RSA information can help improve AT detection sensitivity and specificity, thereby reducing healthcare cost associated with false AT detections. Additionally, the improvements in AT detection can be achieved with little to no additional cost or added system complexity. In some examples, existing system performance can be maintained (e.g., high arrhythmia detection sensitivity and specificity, etc.) using lower cost or less obtrusive systems, apparatus, and methods. With improved AT detection, fewer alarms are provided, battery life can be extended, fewer unnecessary drugs and procedures may be scheduled, prescribed, or provided, and an overall system cost and power savings may be realized in contrast to existing medical devices and systems.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a physiologic event detector circuit 160 configured to detect a physiologic event using the sensed physiologic signals. In an example, the physiologic event includes a cardiac arrhythmia episode, such as an episode of atrial fibrillation, atrial flutter, atrial tachycardia, supraventricular tachycardia, ventricular tachycardia, or ventricular fibrillation, cardiac pauses, among other brady- or tachy-arrhythmia. In some examples, the physiologic event detector circuit 160 is configured to detect worsening of a chronic medical condition, such as worsening heart failure (WHF). The physiologic event detector circuit 160 may execute a detection algorithm to monitor one or more physiologic signals continuously or periodically, and to detect the physiologic event automatically. Additionally or alternatively, the physiologic event detector circuit 160 may be configured to operate in a patient-triggered mode, register a patient-triggered episode and record physiologic data in response to a user-activated trigger. The trigger may be activated by the patient when the patient demonstrates certain signs or symptoms, or experiences a precursor event indicative of a medical event.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer or a mobile device. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or FEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event episodes, may be collected by the AMD 110, among other data acquisition sensors or devices associated with the patient 102. The remote device 124 may include a storage unit to store the patient data in a patient database. The storage unit may additionally store an association between a plurality of episode characterizations and a plurality of detection algorithms for detecting a medical event having respective episode characterizations. The server may process the device-generated event episodes to verify that a specific medical event (e.g., a cardiac arrhythmia type) is detected such that the device-detected event is a true positive (TP) detection; or that no such medical event is detected such that the device-detected event is a false positive (FP) detection. The processing of the device-generated medical event episodes may be based on a stored association. In an example, a first event episode may be presented to a user (e.g., a clinician), who would provide an adjudication decision and a first episode characterization. If the adjudication decision indicates that the first event episode is a FP detection, then the server may identify from the stored association a detection algorithm corresponding to the first episode characterization, and process a second event episode using at least the identified detection algorithm to determine that the second event episode is either a TP or a FP detection. The server may schedule a presentation of at least a portion of the second episode using the processing result of the second episode. By using the detection algorithms tailored for recognizing episode with an episode characterization associated with a FP episode, more FP episodes having the same or similar episode characterization may be identified, and therefore avoided from being reviewed and adjudicated by the user. If the second event episode is determined to be a TP episode, then an alert is generated indicating further user review may be warranted.

By way of example, alert notifications may include a Web page update, phone or pager call, E-mail, SMS, text or "Instant" message, as well as a message to the patient and a simultaneous direct notification to emergency services and to the clinician. Other alert notifications are possible. In some examples, the server may include a medical event prioritizer circuit configured to prioritize the alert notifications. For example, an alert of a detected medical event may be prioritized using a similarity metric between the physiologic data associated with the detected medical event to physiologic data associated with the historical alerts.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic or functional signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the medical events. Computationally intensive algorithms, such as machine-learning algorithms, may be implemented in the external data processor to process the data retrospectively to detect cardia arrhythmia.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

FIG. 2 illustrates generally an example of an arrhythmia detection system 200 configured to detect an arrhythmia episode, such as an AT episode. Portions of the arrhythmia detection 200 may be included in the physiologic event detector circuit 160 of the AMD 110. The arrhythmia detection system 200 may include one or more of a sensor circuit 210, an arrhythmia detector circuit 230, and a user interface unit 240. The arrhythmia detection system 200 may additionally include an optional therapy circuit 250.

The sensor circuit 210 may include a sense amplifier circuit to sense a physiologic signal from a patient via one or more implantable, wearable, or otherwise ambulatory sensors or electrodes associated with the patient. The sensor circuit 210 may include one or more other sub-circuits to digitize, filter, or perform other signal conditioning operations on the sensed physiologic signal. Examples of the physiologic signals may include surface electrocardiography (ECG) such as sensed from electrodes on the body surface, subcutaneous ECG such as sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others.

In an example as illustrated in FIG. 2, the sensor circuit 210 may include a heart beat sensor 211 and a respiration sensor 212. The heart beat sensor 211 can include one or more implantable, wearable, or otherwise ambulatory cardiac activity sensor configured to sense cardiac electrical or mechanical activity from the patient. Examples of the cardiac electrical activity may include an ECG sensed using surface electrodes or subcutaneous electrodes, or intracardiac EGM sensed from inside the heart chamber or heart tissue using intracardiac electrodes. Examples of cardiac mechanical activity may include a heart sounds (HS) signal such as sensed using an accelerometer or a microphone to sense cardiac vibrational or acoustic information, a cardiac impedance signal that varies with cyclic cardiac contractions which can be sensed using an impedance sensor, or a pressure signal that varies with arterial pulses which can be sensed using a pressure sensor, among others. The heart beat sensor 211 can detect one or more heart beats, or one or more arterial pulses, from the sensed cardiac electrical or mechanical activity, and determine one or more heart rates (HR) or cardiac cycle lengths (CLs).

The respiration sensor 212 can be configured to sense a respiration signal, Resp(t), from the patient, where "t" denotes time. The respiration signal may be sensed concurrently with the heart beats. The respiration sensor 212 may be coupled to electrodes attached to or implanted in the patient to sense the respiration signal from the patient. The respiration signal includes a respiration waveform that represents the change of airflow or lung volume during a respiratory cycle. The respiration sensor may include a flowmeter configured to sense directly the airflow in the respiratory system or volume change in the lungs. Alternatively, the respiration sensor may sense a physiological signal modulated by respiration, such as a thoracic impedance signal. The thoracic impedance may be measured using electrodes on an implantable lead coupled to an implantable medical device. In an example, the thoracic impedance may be sensed between an electrode on a right ventricular and the can housing of and implantable device implanted at the left or right pectoral region. In another example, the thoracic impedance may be sensed between an electrode on a left ventricle and the can housing of the implantable device, or between a right atrium electrode and the can housing of the implantable device. The thoracic impedance may alternatively be measured using non-invasive surface electrodes removably attached to a patient chest. In some examples, the respiration sensors may sense other respiration-modulated physiological signals including, for example, chest muscle strain sensor to measure cyclic changes in muscle tension corresponding to respiration cycles, accelerometers to measure acceleration associated with displacement or movement of chest walls corresponding to respiration, or acoustic or vibrational signals modulated by respiration. The respiration sensors may alternatively include patient-external respiratory bands, respiration flowmeter, implantable or patient-external breath sound detector, blood oxygen level detector, and other sensors configured to sense a respiration-modulated physiological signal, which can be found in Lee et al., U.S. Pat. No. 7,678,061 entitled "System and method for characterizing patient respiration", filed on Apr. 15, 2004, which is incorporated herein by reference in its entirety.

In some examples, the physiologic signals may be stored in a storage device such as an electronic medical record system. The sensor circuit 210 may retrieve a physiologic signal from the storage device in response to a command signal that is provided by a system user, or automatically generated in response to occurrence of a specific event.

The arrhythmia detector circuit 230 may detect an indication of RSA, and use the RSA indication to detect an AT episode. The arrhythmia detector circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The arrhythmia detector circuit 230 may include circuit sets comprising one or more other circuits or sub-circuits, including an RSA detector 232 and an atrial tachyarrhythmia detector 234. These circuits or sub-circuits may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, movable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The RSA detector 232 may be configured to determine an RSA indictor using the heart rates or cycle lengths sensed by the heart beat sensor 211 and the respiration signal Resp(t) sensed by the respiration sensor 212. In an example, the RSA detector 232 may include a signal conditioning circuit to resample (e.g., interpolate) the sensed heart rates or cycle lengths to generate a heart rate or cycle length signal, HR(t), where "t" denotes time. The HR(t) signal is a time series of instantaneous HRs or CLs. The signal conditioning circuit can further filter the HR(t) signal to extract a respiration component. By way of non-limiting example, HR(t) may be filtered through a low-pass filter with a cutoff frequency of approximately 1 Hz, or a bandpass filter with a passband of approximately 0.05-1 Hz. Such a filter can substantially attenuate cardiac contractile activity and other high-frequency interferences, and preserve the respiration component. The filtered signal, $HR_{Resp}(t)$, represents a degree of respiration modulation of the heart rates or cycle lengths.

The RSA detector 232 may compare the sensed respiration signal Resp(t) to the filtered HR signal, $HR_{Resp}(t)$, to determine a presence or absence of RSA. In an example, a signal conditioning circuit can preprocess the Resp(t) signal, such as filtering it to remove high-frequency noise or interferences. Examples of the filters may include a low-pass filter with a cutoff frequency of approximately 1 Hz, or a bandpass filter with a passband of approximately 0.05-1 Hz. The RSA detector 232 may generate an RSA indicator indicating contribution of respiration to the temporal variation of heart rates or cardiac cycle lengths via a mechanism of RSA. In an example, the RSA indicator may be represented by a correlation between Resp(t) and $HR_{Resp}(t)$. The correlation can take values in a range from −1 to 1, where "−1" indicates an inverse relationship of opposite directions of variation between the two signals, "1" indicates that the two signals co-vary in the same direction, and "0" indicates no association between the two signals. A high correlation that exceeds a specific correlation threshold may indicate a presence of RSA, or that the RSA contributes significantly to the HR or CL variability. The detected irregular heart rates may be more attributable to RSA than to an AT episode. Conversely, a low correlation below the specific correlation threshold indicates an absence of RSA, or that the RSA contributes insignificantly to the HR or CL variability. The detected irregular heart rates may be less attributable to RSA, but more likely due to ongoing atrial tachyarrhythmia. In an example, the correlation threshold is approximately 0.6-0.8.

In addition to or in lieu of the correlation discussed above, the RSA detector 232 may generate the RSA indicator using a comparison of one or more temporal, statistical, or spectral features respectively generated from the Resp(t) and $HR_{Resp}(t)$ signals. In an example, inter-breath intervals (IBIs) may be measured respectively from the Resp(t) and $HR_{Resp}(t)$, and the RSA indicator may be computed using a similarity or concordance between the IBIs corresponding to Resp(t) and the IBIs corresponding to $HR_{Resp}(t)$. If the computed similarity or concordance exceeds a specific threshold, RSA is determined to be present and contribute significantly to the HR or CL variability. Otherwise, the RSA indicator indicates an absence of RSA, or that the RSA contributes insignificantly to the HR or CL variability. In another example, zero-crossings of the Resp(t) and $HR_{Resp}(t)$ signals during a specified time period can be determined and compared to each other. The RSA indicator may be represented by a similarity of timings and/or counts of zero-crossings corresponding to Resp(t) and timings and/or counts of zero-crossings corresponding to $HR_{Resp}(t)$. If the computed similarity exceeds a specific threshold, RSA is determined to be present and contribute significantly to the HR or CL variability. Otherwise, RSA is absent or that the RSA contributes insignificantly to the HR or CL variability.

The AT detector 234 can detect an AT episode, such as an AF or AFL episode, using received physiologic information and the RSA indictor produced by the RSA detector. The AT detector 234 may generate a signal metric (X) using heart beat information sensed by the heart beat sensor 211. Examples of the signal metric X may include heart rates or cardiac cycle lengths, or heart rate or cycle length variability. Additionally or alternatively, the AT detector 234 may generate a signal metric (X) using physiologic information sensed by other sensors 213, separate and different from the heart beat information sensed by the heart beat sensor 211. Examples of such sensors 213 may include pressure sensor, impedance sensor, or heart sound sensor, among others. In an example, the signal metric (X) may include morphological features take from a cardiac electrical or mechanical signal, such as ECG or EGM, pressure, impedance, or heart sounds signals.

In various examples, the signal metric X may include a statistical measure of ventricular heart rates or cycle lengths. One example of the statistical measure includes a ventricular rate pattern of consecutive decrease in ventricular rate. The ventricular rate pattern includes a pair of consecutive ventricular rate changes. Both ventricular rate changes are negative, referred to as a "double decrement" ventricular rate pattern. A double-decrement ratio, which represents a prevalence of the double decrement ventricular rate pattern over a specified time period or over a plurality of ventricular beats, may be computed, and used to detect AT (e.g., AF), or to distinguish AT from ectopic beats. The arrhythmia detector circuit 230 may determine a count of double-decrement beat pattern, or a double-decrement ratio. Such a baseline double-decrement pattern of ventricular rate may distinguish frequent premature ventricular contractions (PVCs) from an AT event, because PVCs alone typically do not produce double decrement patterns in ventricular rate. Krueger et al. U.S. patent application Ser. No. 14/825,669, entitled "ATRIAL FIBRILLATION DETECTION USING VENTRICULAR RATE VARIABILITY," refers to double decrement pattern in ventricular heart rate and its use in atrial arrhythmia detection, the disclosure of which is incorporated by reference herein in its entirety.

Another example of the statistical measure includes a ventricular rate cluster, represented by a statistical distribution or a histogram of ventricular rate or cycle length over multiple cardiac cycles. The ventricular rate cluster indicates regularity of ventricular rates of cardiac cycle lengths. Patients with AF are typically presented with irregular ventricular contractions. However, premature atrial contractions (PACs) may occur at irregular intervals. When PACs conduct to the ventricle, they may produce irregular ventricular rates, resulting in different ventricular clusters than AF. As such, the ventricular rate clusters may be used to distinguish frequent PACs from an AF event. Perschbacher et al. U.S. patent application Ser. No. 15/864,953 entitled "ATRIAL FIBRILLATION DISCRIMINATION USING HEART RATE CLUSTERING," refers to histogram clusters of ventricular rates and their use in discriminating between AF and non-AF events, the disclosure of which is incorporated by reference herein in its entirety.

Yet another example of the statistical measure includes a metric representing the occurrence of various beat patterns of the cycle lengths or heart rates. For example, the beat pattern may include a number or percentage of consecutive heart beats with each time period (e.g., a 2-minute time windows) that are within +/−5 bpm. In an example, the statistical measure includes an atrioventricular (AV) conduction block metric indicating a presence or degree of conduction abnormality during a sinus rhythm, such as a Wenckebach score representing the prevalence of Wenckebach block over a time period. Examples of the Wenckebach detector may be based on a repetitiveness indictor of various beat patterns of the cycle lengths or heart rates, such as discussed in Perschbacher et al. U.S. patent application Ser. No. 15/786,824 entitled "SYSTEMS AND METHODS FOR ARRHYTHMIA DETECTION," the disclosure of which is incorporated by reference herein in its entirety. Other examples of the statistical measure may include a signal morphology metric representing regularity of ventricular depolarization signal morphology during sinus rhythm, or a signal quality metric such as a signal-to-noise (SNR). The signal quality or signal morphology indicator may differentiate the AF from noise.

The AT detector 234 may detect an AT episode by determining if the signal metric X satisfies an arrhythmia detection criterion. In an example, the AT detector 234 may determine the arrhythmia detection criterion (e.g., a threshold for the signal metric X, or a detection duration) using the RSA indicator generated by the RSA detector 232. Additionally or alternatively, the RSA indicator may be used to identify a signal portion of the received physiologic information (heart beats or other physiologic signal) used for generating the signal metric X. Examples of detecting AT using the RSA indicator are discussed below, such as with reference to FIGS. 3A-3D.

The user interface unit 240 may include an input device and an output device. In an example, at least a portion of the user interface unit 240 may be implemented in the external system 130. The input device may receive a user's programming input, such as parameters for adjusting detection criterion and parameters for detecting cardiac arrhythmia. The input device may include a keyboard, on-screen keyboard, mouse, trackball, touchpad, touch-screen, or other pointing or navigating devices. The input device may enable a system user to program the parameters used for sensing the physiologic signals, detecting the arrhythmias, and generating alerts, among others.

The output device may generate a human-perceptible presentation of the detected cardiac arrhythmia. The output device may include a display for displaying the sensed physiologic information, intermediate measurements or computations such as RSA indicator, and the detected AT episodes, among others. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected arrhythmic events.

The optional therapy circuit 250 may be configured to deliver a therapy to the patient in response to the detected cardiac arrhythmia. Examples of the therapy may include electrostimulation therapy delivered to the heart, a nerve tissue, other target tissues, a cardioversion therapy, a defibrillation therapy, or drug therapy. In some examples, the therapy circuit 250 may modify an existing therapy, such as adjust a stimulation parameter or drug dosage.

Figure 3A:
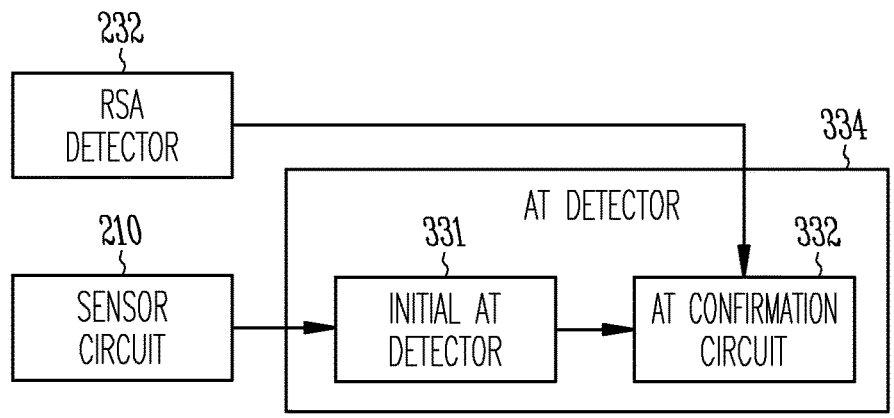
FIGS. 3A-3D are diagrams illustrating examples of portions of an arrhythmia detection medical-device system configured to detect atrial tachyarrhythmia using indications of RSA in a patient.

FIGS. 3A-3D are diagrams illustrating examples of portions of an arrhythmia detection medical-device system configured to detect atrial tachyarrhythmia using indications of RSA in a patient. The illustrated examples can each be implemented in the arrhythmia detection system 200. FIG. 3A illustrates a system portion that uses RSA indicator to confirm a detected AT episode. The system portion includes an AT detector 334, coupled to the RSA detector 232 and the sensor circuit 210, which is an embodiment of the AT detector 234. The AT detector 334 can include an initial AT detector 331 and an AT confirmation circuit 332. The initial AT detector 331 can be configured to generate an initial detection of AT using the sensed physiologic information. In an example, the initial AT detector 331 may generate a signal metric (X). As discussed above, the signal metric X may include ventricular heart rates or cardiac cycle lengths, heart rate or cycle length variability, a statistical measures of ventricular heart rates or cycle lengths, or a signal morphology metric of a ventricular activity signal (e.g., ECG or ventricular EGM). The initial AT detector 331 may determine if the signal metric X satisfies a pre-determined detection criterion, such as a pre-determined threshold, to determine a presence or absence of an AT episode. If the signal metric X satisfies the pre-determined detection criterion (e.g., exceeds the pre-determined threshold), then the AT confirmation circuit 332 may confirm or reject the initial AT detection using the RSA indicator provided by the RSA detector 232. In an example, the initial AT detection can be confirmed if the RSA indicator indicates an absence of RSA, or be rejected if the RSA indicator indicates a presence of RSA.

Figure 3B:
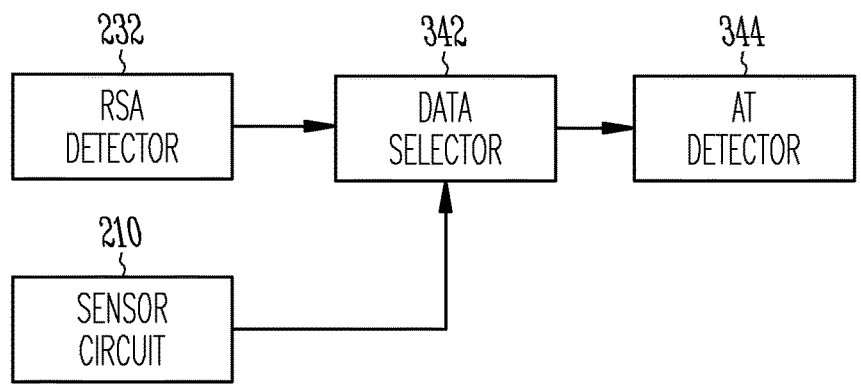

FIG. 3B illustrates a system portion that uses RSA indicator to select a signal portion for use to detect an AT episode. The system portion includes a data selector 342, and an AT detector 344 which is an embodiment of the AT detector 234. The data selector 342, coupled to the RSA detector 232 and the sensor circuit 210, is configured to use the RSA indicator to select a signal portion from the physiologic information received from the sensor circuit 210, where the AT detector 344 can use the selected signal portion to detect an AT episode. In an example, the RSA detector 232 may determine RSA indicators respectively for multiple temporally separated portions of the concurrently acquired respiration information and heartbeats information. The data selector 342 may identify from a received physiologic signal (S) which can be a heart beat signal or other physiologic signal) one or more portions temporally corresponding to the RSA indicators indicating an absence of RSA, and the AT detector 344 may then detect the AT episode using the identified one or more portions of the signal S(t). For example, an RSA indicator, RSA(i), may be generated using concurrently sensed respiration signal segment Resp(i) and heart rates segment HR(i), where "i" denotes i-th signal segments. If RSA(i) indicates a presence of RSA, then the data selector 342 may reject the signal segment S(i), a segment of signal S(t) that temporally corresponds to Resp (i) and HR(i). Consequently, the AT detector 344 would not use S(i) to generate a signal metric X for detecting AT. Conversely, if RSA(i) indicates absence of RSA, then the signal segment S(i) will be selected, and the AT detector 344 can use S(i) to generate a signal metric X for detecting AT. Because signal portions associated with RSA are rejected, data quality can be improved, and less interference or confounding factors will be introduced to the AT detection. As a result, AT detection reliability can be improved.

Figure 3C:
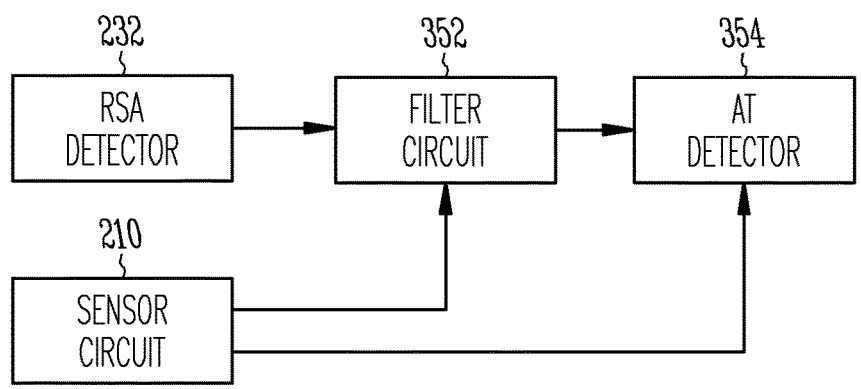

FIG. 3C illustrates a system portion that uses RSA indicator to filter a physiologic signal used for detecting an AT episode. The system portion includes a filter circuit 352 and an AT detector 354 which is an embodiment of the AT detector 234. If the RSA indicator indicates a presence of RSA, then the filter circuit 352 can filter a received physiologic signal S(t) to remove, or attenuate, the effect of RSA on signal S(t). In an example, the filter circuit 352 includes an adaptive filter than can change one or more filter coefficients over time, to adapt to changing characteristics of RSA. In an example, the RSA detector 232 may continuously or periodically generate an RSA characteristic using the respiration signal and the heart beat information, if the RSA indicator indicates a presence of RSA. Examples of the RSA characteristic can include a measure of ventricular heart rate variability during a respiratory cycle. In some examples, the RSA detector 232 can generate the RSA characteristic under a specified patient condition, such as a specific posture (e.g., supine), a specific physical activity level (e.g., rest), or a specific time of day.

The filter circuit 352 may adaptively update filter coefficients using the RSA characteristic. Examples of the adaptive filters may include least mean square (LMS), normalized least mean square (NLMS), or other stochastic gradient descent-based algorithms, Recursive least square (RLS), Kalman filters, among others. In an example, the adaptive filter coefficients can be determined once a convergence condition is met. The received physiologic signal S(t) can be filtered through the adaptive filter, and the AT detector 354 can detect AT using the filtered signal S'(t). Through the adaptive filter, signature of RSA can be substantially removed from the signal S(t). In an example where AT detection is based on heart rate or cycle length variability, by adaptive filtering, contributions of RSA to the HR or CL variability can be substantially reduced, such that the HR or CL variability in the filtered signal can be more reliably be detected and determined to be attributable to an AT episode.

Figure 3D:
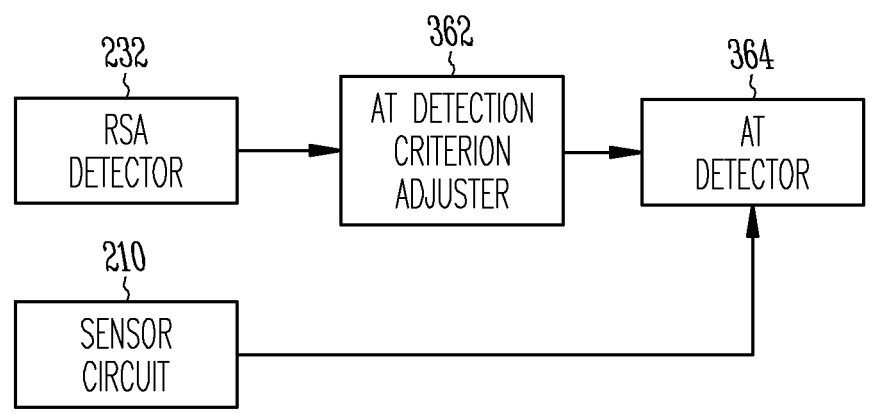

FIG. 3D illustrates a system portion that uses RSA indicator to adjust an AT detection criterion used for detecting an AT episode. The system portion includes an AT detection criterion adjuster 362, and an AT detector 364 which is an embodiment of the AT detector 234. The AT detection criterion adjuster 362 can update an AT detection criterion if the RSA indicator indicates a presence of RSA, and the AT detector 364 can detect an AT episode using the received physiologic information and the updated AT detection criterion. In an example, the AT detection criterion includes a threshold value of a signal metric X, such as ventricular heart rates or cardiac cycle lengths, heart rate or cycle length variability, or one of a variety of statistical measures of ventricular heart rates or cycle lengths, as discussed above with reference to FIG. 2. The AT detector 364 can determine that an AT episode has been detected if the signal metric X exceeds the threshold value of the signal metric. In an example, the signal metric X includes a ventricular heart rate variability, and the AT detection criterion includes a heart rate variability threshold. The AT detection criterion adjuster 362 can increase the heart rate variability threshold if the RSA indicator indicates a presence of RSA, or to decrease the heart rate variability threshold if the RSA indicator indicates an absence of RSA. The AT detector 364 can determine that an AT episode has been detected if the ventricular heart rate variability exceeds the threshold value of the signal metric. Because an AT event generally cause a higher variability of ventricular heart rates than RSA, raising the threshold of heart rate variability above the variability level attributable to RSA may avoid or reduce false positive detections of RSA as an AT episode. Accordingly, a higher AT detection specificity can be achieved.

In another example, the AT detection criterion may include a detection duration (Dur). The AT detector 364 can detect a sustained AT episode if a signal metric X satisfies a detection criterion (e.g., exceeding a threshold) consistently during the specified time duration (Dur). The duration requirement is to ensure the detected AT episode is a sustained AT event, as opposed to a non-sustained event that less likely requires intervention. The AT detection criterion adjuster 362 may adjust the duration using the RSA indicator. In an example, the AT detection criterion adjuster 362 can increase the detection duration if the RSA indicator indicates a presence of RSA, or to decrease the duration if the RSA indicator indicates an absence of RSA. Extending the detection duration Dur in the presence of RSA can help avoid or reduce false positive detections of RSA as an AT episode. The AT detector 364 can determine that a sustained AT episode has been detected if the signal metric X consistently satisfies the detection criterion for at least the detection duration (Dur).

Figure 4:
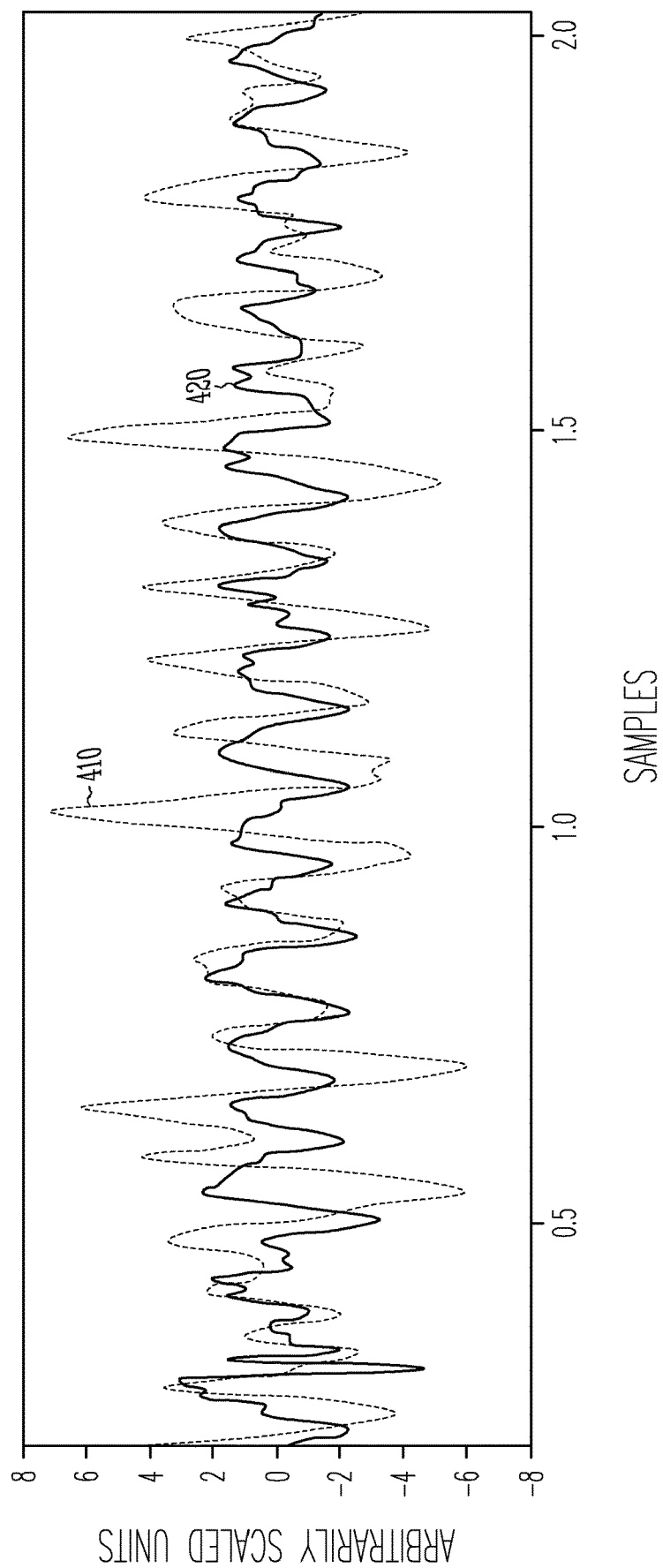
FIG. 4 is a graph illustrating temporal relationship between a portion of a HR-derived respiration signal and a portion of a respiration signal.

FIG. 4 is a graph illustrating temporal relationship between a portion of a HR-derived respiration signal 410 and a portion of a respiration signal 420. A raw HR time series and a raw respiration signal were concurrently sensed from the same patient. As discussed above with reference to FIG. 2, the raw HR time series can be resampled, and filtered through a filter with a specified pass-band (e.g., 0.5-1 Hz), to produce the HR-derived respiration signal 410, denoted by $HR_{Resp}(t)$, which represents the modulating respiration component in the HR time series. $HR_{Resp}(t)$ can indicate a presence of RSA. The independently sensed raw respiration signal can be filtered using a filter with a specified pass-band (e.g., 0.5-1 Hz). The resulting respiration signal 420 can be compared to the HR-derived respiration signal 410 to confirm the presence of RSA, as discussed above with reference to FIG. 2. In the example of FIG. 4, the HR-derived respiration signal 410 and the respiration signal 420 co-vary in phase over multiple respiratory cycles, indicating a tight coupling. Accordingly, the RSA detector 232 can determine that a high correlation exists between $HR_{Resp}(t)$, and Resp(t), and that RSA is present.

Figure 5:
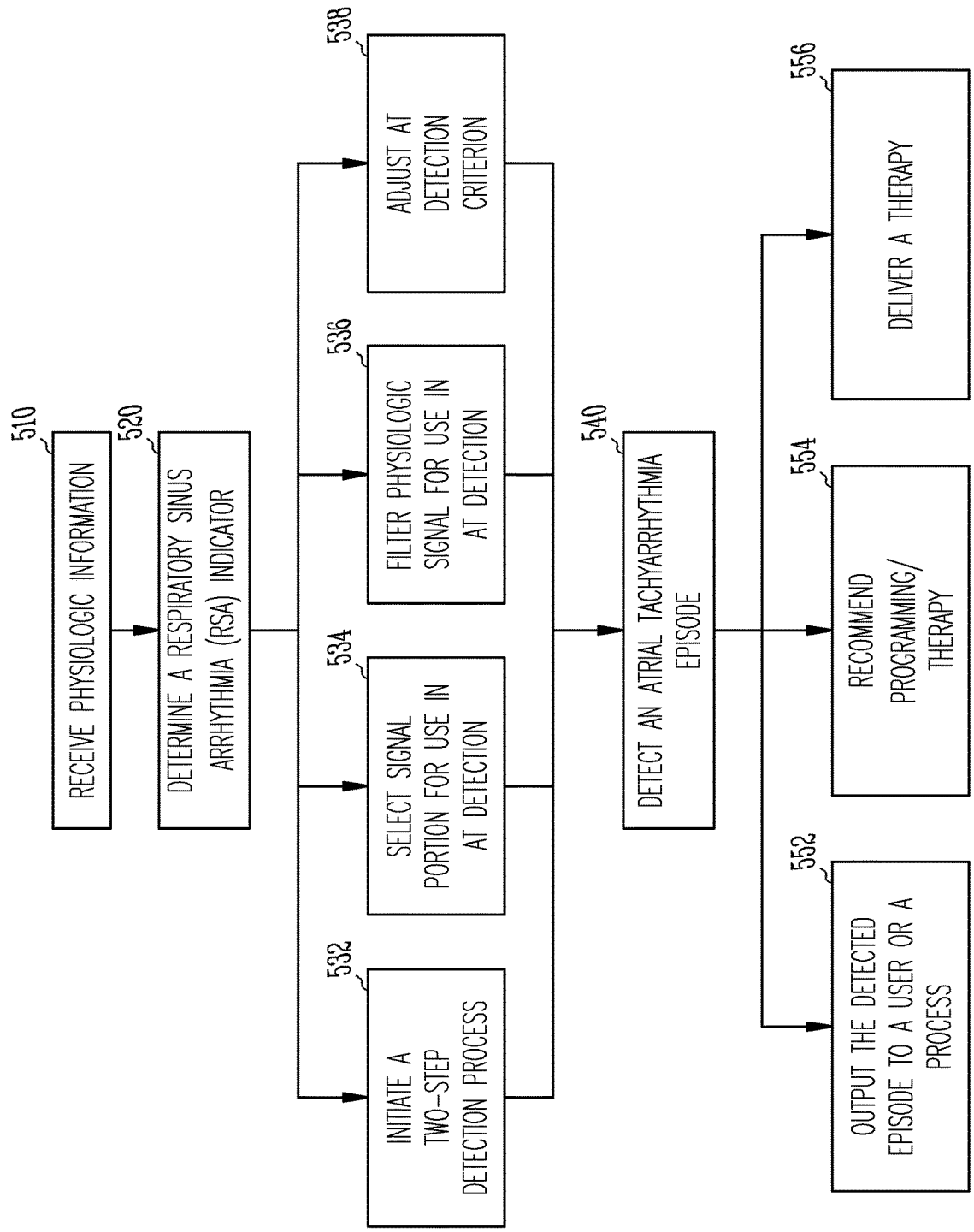
FIG. 5 is a flowchart illustrating an example of a method for detecting atrial tachyarrhythmia in a patient.

FIG. 5 is a flow chart illustrating an example of a method 500 for detecting atrial tachyarrhythmia in a patient. Examples of atrial tachyarrhythmia may include atrial fibrillation (AF), atrial flutter (AFL), atrial tachycardia, among others. The method 500 may be implemented and executed in an ambulatory medical device such as an implantable or wearable medical device, or in a remote patient management system. In an example, the method 500 may be implemented in and executed by the cardiac arrhythmia detection circuit 160 in the AMD 110, the external system 130, or the arrhythmia detection system 200.

The method 500 commences at 510, where physiologic information of a patient may be received. The physiologic information may be sensed from physiologic sensors associated with a patient, or be retrieved from a storage device (e.g., an electronic medical record system) that stores physiologic signals recorded from a patient. The physiologic signal may include a cardiac electrical signal such as an ECG or an intracardiac EGM, thoracic or cardiac impedance signal, arterial pressure signal, pulmonary artery pressure signal, left atrial pressure signal, RV pressure signal, LV coronary pressure signal, heart sounds or endocardial acceleration signal, physiologic response to activity, apnea hypopnea index, one or more respiration signals such as a respiration rate signal or a tidal volume signal, among others. The sensed physiologic signal may be pre-processed, including one or more of signal amplification, digitization, filtering, or other signal conditioning operations.

At 520, a respiratory sinus arrhythmia (RSA) indicator may be generated using the received physiologic information. The RSA indicator indicates a presence or absence of RSA. The generation of the RSA indication may involve heart rates or cycle lengths, and respiration information concurrently acquired from the same patient. The heart rates or cycle lengths may be resampled (e.g., interpolated) to produce a heart rate or cycle length signal, HR(t), representing instantaneous heart rates or cycle lengths over time. The HR(t) signal can be filtered through a low-pass filter with a cutoff frequency of approximately 1 Hz, or a bandpass filter with a passband of approximately 0.05-1 Hz, to extract a respiration component. The filtered signal, $HR_{Resp}(t)$, represents a degree of respiration modulation of the heart rates or cycle lengths. An RSA indicator can then be generated using a comparison between the filtered HR signal, $HR_{Resp}(t)$ and a concurrently sensed respiration signal Resp(t). In an example, the RSA indicator may be represented by a correlation between Resp(t) and $HR_{Resp}(t)$. A high correlation, such as one that exceeds a specific correlation threshold, indicates a presence of RSA, or that RSA contributes significantly to the heart rate variability or the cycle length variability. In various examples, the RSA indicator may alternatively be generated using a comparison of one or more temporal, statistical, or spectral features respectively generated from the Resp(t) and $HR_{Resp}(t)$ signals, such as inter-breath intervals (IBIs) or zero-crossings measured respectively from the Resp(t) and $HR_{Resp}(t)$, and RSA indicator may be computed using a similarity or concordance between the IBIs of the Resp(t) and $HR_{Resp}(t)$, or between the zero-crossing of the Resp(t) and $HR_{Resp}(t)$. RSA is determined to be present and contribute significantly to the heart rate or cycle length variability if the computed similarity exceeds a specific threshold, or absent and has insignificant contribution to the heart rate or cycle length variability if the computed similarity falls below the specific threshold.

The RSA indicator can be used to detect atrial tachyarrhythmia (AT) in one or more methods 532, 534, 536, or 538. At 532, the detection of RSA at 520 may trigger a two-step process for detecting an AT episode, which includes an initial AT detection, followed by a confirmation or rejection of the initial AT detection based on the RSA indication. As discussed above with reference to FIG. 3A, the initial detection may include generating a signal metric X, such as a ventricular heart rate, heart rate variability, or a statistical measure of ventricular heart rates or cycle lengths (e.g., a ventricular rate cluster, a Wenckebach score, or a double-decrement ratio, as discussed above with reference to FIG. 2). If the signal metric X satisfies a pre-determined detection criterion, such as a pre-determined threshold, an AT episode is deemed detected from the initial AT detection. Then at 540, AT detection can include a process of confirming the initial AT detection if the RSA indicator indicates an absence of RSA, or rejecting the initial AT detection if the RSA indicator indicates a presence of RSA.

Alternatively, at 534, the RSA indicator can be used to select a signal portion from the received physiologic information. As discussed above with reference to FIG. 3B, only signal portions that correspond to RSA indicators indicating an absence of RSA are selected for use in AT detection. Signal portions that correspond to RSA indicators indicating a presence of RSA are not selected for use in AT detection. Such a data selection process can improve quality of the physiologic data to be used for detecting AT, and the AT detection reliability can be improved. At 540, a signal metric may be generated from the selected portion of the received physiologic information, and an AT episode can be detected using the generated signal metric.

Alternatively, at 536, the RSA indicator can be used to filter a physiologic signal used for detecting an AT episode. As discussed above with reference to FIG. 3C, a received physiologic signal can be filtered to remove, or attenuate, the effect of RSA on the received signal. In an example, the filter can include an adaptive filter with one or more filter coefficients being variable over time to adapt to changing characteristics of RSA. Examples of the RSA characteristic can include a measure of ventricular heart rate variability during a respiratory cycle. In some examples, the RSA detector 232 can generate the RSA characteristic under a specified patient condition, such as a specific posture (e.g., supine), a specific physical activity level (e.g., rest), or a specific time of day. At 540, an AT episode can be detected using the filtered physiologic signal.

Alternatively, at 538, the RSA indicator can be used to adjust an AT detection criterion used for detecting an AT episode. As discussed above with reference to FIG. 3D, an example of the AT detection criterion is a detection threshold for a signal metric X, such as ventricular heart rates or cardiac cycle lengths, heart rate or cycle length variability, one of a variety of statistical measures of ventricular heart rates or cycle lengths, or a signal morphology metric of a ventricular activity signal (e.g., ECG or ventricular EGM). In an example, the signal metric X includes a ventricular heart rate variability, and the AT detection criterion includes a heart rate variability threshold. At 538, the heart rate variability threshold can be adjusted such that said threshold can be increased if the RSA indicator indicates a presence of RSA, or be decreased if the RSA indicator indicates an absence of RSA. In another example, the detection criterion can include a duration (Dur) parameter for detecting a sustained AT episode. The duration parameter can be adjusted according to the presence or absence of RSA. At 540, an AT episode can be detected using the adjusted AT detection criterion, such as an adjusted threshold value of the signal metric X.

An AT episode can be detected at 540 using the received physiologic information and the RSA indicator, where the physiologic information (or other information such as detection criterion) may be processed following one or more of the steps 532, 534, 536, or 538. An AT episode is detected if a signal metric X satisfies a detection criterion, such as a detection threshold. The detected AT episode may be used in one or more of the processes 552, 554, or 556. At 552, the detected AT episode may be output to a user or a process, such as via the user interface 240 illustrated in FIG. 2. In an example, information may be displayed on a display, including the physiologic signal, extracted signal features, the SR template, the morphologic similarity metric and the morphologic variability metric, the detection decision of the atrial tachyarrhythmia episode, among others. Alternatively or additionally, at 554, a recommendation may be generated and provided to the user, such as performing further diagnostic tests, initiating anti-arrhythmic therapy to treat the detected arrhythmia or to alleviate the arrhythmic complications, or adjusting one or more arrhythmia detection parameters. A system user may review and adjudicate the detected atrial tachyarrhythmia episode, and reprogram one or more detection parameters.

The method 500 may include the optional step 556 of delivering a therapy to the patient in response to the detection of the cardiac arrhythmia, such as via the optional therapy circuit 250 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia, such as modify patient follow-up schedule, or adjust a stimulation parameter or drug dosage.

Figure 6:
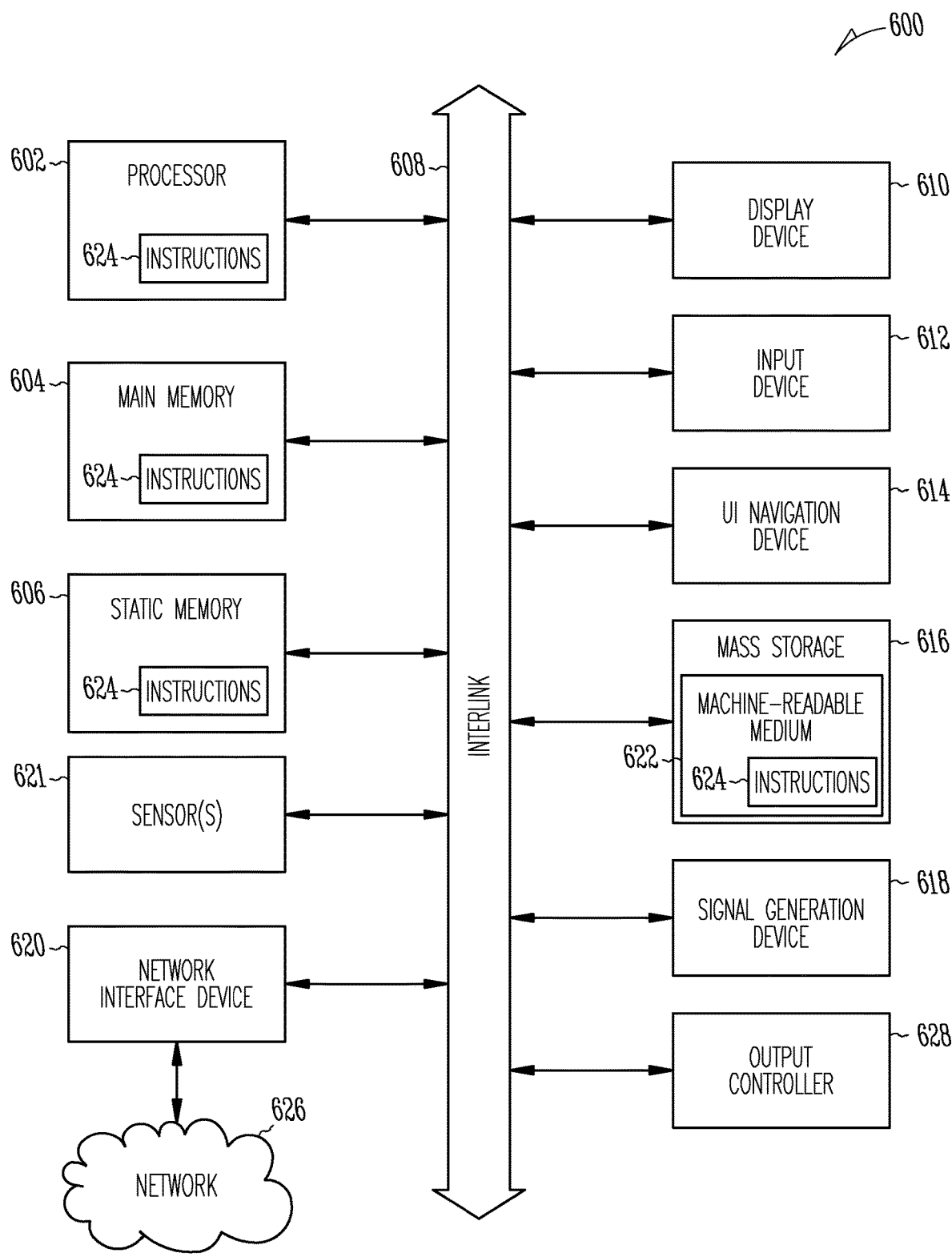
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, movable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system for detecting cardiac arrhythmia, comprising:
    an arrhythmia detector circuit configured to:
        receive respiration information and heart beat information from a patient;
        determine whether a respiratory sinus arrhythmia (RSA) is present or absent using the received respiration information and the received heart beat information;
        determine or adjust an arrhythmia detection algorithm based on the presence or the absence of RSA; and
        detect an atrial tachyarrhythmia (AT) episode using the determined or adjusted arrhythmia detection algorithm.

2. The system of claim 1, wherein the arrhythmia detector circuit is configured to:
    perform an initial AT detection using the received heart beat information; and
    confirm the initial AT detection if the RSA is absent, or reject the initial AT detection if the RSA is present.

3. The system of claim 1, wherein to determine or adjust the arrhythmia detection algorithm, the arrhythmia detector circuit is configured to select, from a received physiological signal from the patient, a signal portion temporally corresponding to the absence of RSA, and to detect the AT episode using the selected signal portion of the received physiological signal.

4. The system of claim 1, wherein to determine or adjust the arrhythmia detection algorithm, the arrhythmia detector circuit is configured to:
    determine RSA indicators respectively for multiple temporally separated portions of the received respiration information and the received heart beat information;
    identify from received physiologic information one or more portions corresponding to the RSA indicators indicating the absence of RSA; and
    detect the AT episode using the identified one or more portions of the received physiologic information.

5. The system of claim 1, wherein to determine or adjust the arrhythmia detection algorithm, the arrhythmia detector circuit is configured to:
    filter received physiologic information from the patient to attenuate RSA interference using an RSA characteristic; and
    detect the AT episode using the filtered received physiologic information.

6. The system of claim 5, wherein the arrhythmia detector circuit is configured to filter the received physiologic information using an adaptive filter.

7. The system of claim 5, wherein the RSA characteristic includes a heart rate variability.

8. The system of claim 5, wherein the arrhythmia detector circuit is configured to generate the RSA characteristic under a specified patient condition including a specific posture, a specific physical activity, or a specific time of day.

9. The system of claim 1, wherein to determine or adjust the arrhythmia detection algorithm, the arrhythmia detector circuit is configured to adjust an AT detection criterion if the RSA is present, and to detect the AT episode using the adjusted AT detection criterion.

10. The system of claim 9, wherein the AT detection criterion includes a heart rate variability threshold, and wherein the arrhythmia detector circuit is configured to:
    determine a heart rate variability using the received heart beat information;
    increase the heart rate variability threshold if the RSA is present;
    decrease the heart rate variability threshold if the RSA is absent; and
    detect the AT episode using a comparison of the determined heart rate variability and the heart rate variability threshold.

11. The system of claim 1, comprising an accelerometer sensor configured to sense a respiration signal from the patient, and a cardiac activity sensor, separate from the accelerometer sensor, configured to detect heart beats from a cardiac signal of the patient.

12. The system of claim 1, wherein the received respiration information includes a respiration signal, and the arrhythmia detector circuit is configured to:
    generate a heart rate (HR) signal using the received heart beat information, the HR signal including measurements of HR or cardiac cycle length over multiple cardiac cycles;
    determine a correlation between the HR signal and the respiration signal; and
    determine the presence of RSA if the correlation is above a threshold, and the absence of RSA if the correlation is below the threshold.

13. A method of detecting atrial tachyarrhythmia (AT), comprising:
    receiving respiration information and heart beat information from a patient;
    determining whether a respiratory sinus arrhythmia (RSA) is present or absent using the received respiration information and the received heart beat information;
    determining or adjusting an arrhythmia detection algorithm based on the presence or the absence of RSA; and
    detecting an AT episode using the determined or adjusted arrhythmia detection algorithm.

14. The method of claim 13, wherein detecting the AT episode includes:
    performing an initial AT detection using the received heart beat information; and
    confirming the initial AT detection if the RSA is absent, or reject the initial AT detection if the RSA is present.

15. The method of claim 13, wherein determining or adjusting the arrhythmia detection algorithm includes selecting from a received physiologic signal from the patient a signal portion temporally corresponding to the absence of RSA, and wherein detecting the AT episode includes using the selected signal portion of the received physiological signal.

16. The method of claim 13, wherein determining or adjusting the arrhythmia detection algorithm includes filtering received physiologic information to attenuate RSA interference using an RSA characteristic, and detecting the AT episode using the filtered received physiologic information.

17. The method of claim 16, wherein the RSA characteristic includes a heart rate variability under a specified patient condition including a specific posture, a specific physical activity, or a specific time of day.

18. The method of claim 13, wherein determining or adjusting the arrhythmia detection algorithm includes adjusting an AT detection criterion if the RSA is present, and detecting the AT episode using the adjusted AT detection criterion.

19. The method of claim 18, wherein the AT detection criterion includes a heart rate variability threshold, and wherein adjusting the AT detection criterion includes increasing the heart rate variability threshold if the RSA is present, or decreasing the heart rate variability threshold if the RSA is absent.

20. The method of claim 13, wherein the received respiration information includes a respiration signal, the method comprising:

generating a heart rate (HR) signal using the received heart beat information, the HR signal including measurements of HR or cardiac cycle length over multiple cardiac cycles;

determining a correlation between the HR signal and the respiration signal; and determining the presence of RSA if the determined correlation is above a threshold, or the absence of RSA if the determined correlation is below the threshold.

\* \* \* \* \*